United States Patent
Kotzev

(10) Patent No.: US 6,224,622 B1
(45) Date of Patent: May 1, 2001

(54) BIOABSORABLE CYANOACRYLATE TISSUE ADHESIVES

(75) Inventor: Dimiter Lubomirov Kotzev, Alpharetta, GA (US)

(73) Assignee: Chemence, Inc., Alpharettà, GA (US)

( * ) Notice: Subject to any disclaimer, the term of this patent is extended or adjusted under 35 U.S.C. 154(b) by 0 days.

(21) Appl. No.: 09/409,312

(22) Filed: Sep. 29, 1999

(51) Int. Cl.⁷ ................................... A61B 17/08
(52) U.S. Cl. ............................................... 606/214
(58) Field of Search .................. 606/213–216; 526/298, 297, 193, 194; 525/66, 77, 86, 88

(56) References Cited

U.S. PATENT DOCUMENTS

| | | | |
|---|---|---|---|
| 5,994,464 | * 11/1999 | Ohsawa et al. | 525/85 |
| 6,001,345 | * 11/1999 | Askill et al. | 424/78.25 |
| 6,093,780 | * 7/2000 | Attarwala | 526/298 |

* cited by examiner

*Primary Examiner*—Michael H. Thaler
*Assistant Examiner*—(Vikki) Hoa B. Trinh
(74) *Attorney, Agent, or Firm*—Brobeck, Phleger & Harrison, LLP

(57) ABSTRACT

Bioabsorbable cyanoacrylate-based tissue adhesives containing bioabsorbable copolymers are disclosed. The copolymers are preferably derived from ε-caprolactone, lactide and glycolide monomers or from butyl 2-cyanoacrylate, glycolide, lactide, ε-caprolactone monomers. The adhesives are characterized by increased biodegradability, increased viscosity and increased flexibility. The adhesives are useful for wound and incision closure, and for medical devices, including implants.

30 Claims, No Drawings

BIOABSORABLE CYANOACRYLATE TISSUE ADHESIVES

BACKGROUND

1. Field of the Invention

This invention relates to cyanoacrylate tissue adhesives, and more particularly, to bioabsorbable cyanoacrylate tissue adhesive compositions and to methods for making and using these compositions. The compositions are useful in medical applications, including, but not limited to, wound and surgical incision closure, medical device fixation, sealants and void fillers, embolic agents and other general medical applications.

2. Description of the Background

Surgical incisions and wounds may be closed by three general methods, suturing, stapling and adhesive bonding.

U.S. Pat. No. 5,578,046 notes that sutures are bioabsorbable when the material that they are made from is capable of being broken down into smaller constituents, which can be metabolized and excreted by the living organism. Such materials are useful for temporarily holding tissues in a desired position during healing and are absorbed by the organism after a period of time. U.S. Pat. No. 5,578,046 as well as the patents and literature in turn referenced by U.S. Pat. No. 5,578,046 are incorporated herein by reference.

Wound suturing has the advantage of producing bioabsorbable, non-toxic degradation products. However, it also has disadvantages. Suturing requires time and skill. It causes additional trauma to the tissue by piercing and does not provide a hermetic closure.

Cyanoacrylates posses the unique property to bond living tissue. They have been widely and successfully tested for closing wounds and incisions, especially in cases where suturing does not provide satisfactory results. See Lijoi A. et al, "Subacute left ventricular free wall rupture complicating acute myocardial infarction. Successful surgical repair with a sutureless technique", J. Cardiovascular Surgery, 1996 December, 37(6), 627–630; Tebala G. D. et al, "The use of cyanoacrylate tissue adhesive in high-risk intestinal anastomoses", Surgery Today, 1995, 25 (12), 1069–72 and Zaki I. et al, "Split skin grafting on severely damaged skin. A technique using absorbable tissue adhesive", J. of Dermatologic Surgery and Oncology, 1994 December, 20(12), 827–9.

Cyanoacrylate tissue adhesives have the following advantages over suturing: they save time; they can bond difficult to suture tissues; they can provide a hermetic closure; they have hemostatic action; they produce better cosmetic results; and they may be indispensable in emergencies.

A major disadvantage of cyanoacrylate adhesives is that one of the degradation products is formaldehyde, which is toxic to the surrounding tissues (see Pani K. C. et al, "The degradation of n-butyl alpha-cyanoacrylate tissue adhesive. II.", Surgery, 1968 March, 63(3), 481–9). For this reason, cyanoacrylates have not found favor with the FDA for internal tissue closure. Only topical skin closure applications have been FDA approved.

Other disadvantages of cyanoacrylate tissue adhesives are their runniness (low viscosity) in uncured form and stiffness when cured.

SUMMARY OF THE INVENTION

The present invention overcomes the problems and disadvantages associated with current cyanoacrylate adhesives and provides compositions useful as bioabsorbable tissue adhesives. The adhesives of the present invention are quickly biodegradable with reduced formaldehyde generation, and provide hermetic closure and hemostatic action. Additional benefits include increased application viscosity and increased flexibility in the cured state of the adhesives.

One embodiment of the invention is directed to a copolymer derived from one or more cyanoacrylates and one or more other monomers, wherein the one or more cyanoacrylates are selected from the group consisting of alkyl 2-cyanoacrylate, alkenyl 2-cyanoacrylate, alkoxyalkyl 2-cyanoacrylate, and carbalkoxyalkyl 2-cyanoacrylate. The alkyl group of the one or more cyanoacrylates preferably has 1 to 16 carbon atoms, and the one or more other monomers are selected from the group consisting of glycolide, lactide, $\epsilon$-caprolactone, dioxanone and trimethylene carbonate.

Another embodiment is directed to a method for making a bioabsorbable tissue adhesive composition comprising the step of dissolving the above described copolymers into a cyanoacrylate monomer or blend of cyanoacrylate monomers. The cyanoacrylate monomer or monomers are selected from the group consisting of alkyl 2-cyanoacrylate, alkenyl 2-cyanoacrylate, alkoxyalkyl 2-cyanoacrylate, or carbalkoxyalkyl 2-cyanoacrylate. The alkyl group of the cyanoacrylate monomer or monomers preferably has 1 to 16 carbon atoms.

Another embodiment is directed to bioabsorbable tissue adhesives made by this method.

Another embodiment of the invention is directed to a method for making a bioabsorbable tissue adhesive composition comprising the step of dissolving one or more copolymers, the copolymers derived from glycolide and two other monomers, into a cyanoacrylate monomer or blend of cyanoacrylate monomers. The one or more copolymers possess amorphous structure and are in a rubbery state at body temperature. The two other monomers are selected from the group consisting of lactide, $\epsilon$-caprolactone, dioxanone and trimethylene carbonate. The cyanoacrylate monomer or monomers are selected from the group consisting of alkyl 2-cyanoacrylate, alkenyl 2-cyanoacrylate, alkoxyalkyl 2-cyanoacrylate, or carbalkoxyalkyl 2-cyanoacrylate. The alkyl group of the cyanoacrylate monomer or monomers preferably has 1 to 16 carbon atoms.

Another embodiment is directed to bioabsorbable tissue adhesives made by this method.

Other embodiments and advantages of the invention are set forth in part in the description which follows, and in part, will be obvious from this description, or may be learned from the practice of the invention.

DESCRIPTION OF THE INVENTION

As embodied and broadly described herein, the present invention is directed to cyanoacrylate-based tissue adhesives which combine the advantages of bioabsorbable suturing with the advantages of adhesive bonding. The compositions of the present invention are quickly biodegradable with reduced formaldehyde generation, and provide hermetic closure and hemostatic action. Additional benefits of the present invention include increased application viscosity and increased flexibility in the cured state of the adhesives.

The present invention is useful in medical applications, including veterinary and other applications where a biodegradable bond is desired. Compositions of the invention may be used to bond tissue to tissue, tissue to a foreign object such as an implant, or even two foreign objects to each other.

Although lactide—$\epsilon$-caprolactone copolymers have been added to cyanoacrylate for thickening and plasticizing of the resultant polymer with good experimental results (see Tseng Y.-C. et al, "Physical modification of a-cyanoacrylate for application as surgical adhesives", Progress in Biomedical Polymers, Ed. By C. G. Gebelein and R. L. Dunn, Plenum Press, New York, 1990, pp. 53–63), the lactide—$\epsilon$- caprolactone copolymer is not as easily biodegradable as glycolide-based copolymers and not easily soluble into cyanoacrylate at high concentrations.

In contrast, the present invention provides for an adhesive bond with enhanced biodegradability.

One embodiment of the present invention utilizes novel biodegradable copolymers derived from cyanoacrylate and one or more of the following monomers: glycolide, lactide, ε-caprolactone, dioxanone, and trimethylene carbonate. The cyanoacrylate moiety of the novel copolymers renders them easily soluble in a wide range of proportions into cyanoacrylate monomers, yielding adhesives with high viscosity in uncured state and high flexibility in cured state. The adhesives have an enhanced bioabsorbability profile with non-toxic degradation products and a reduced amount of formaldehyde.

The present invention includes two different types of copolymers as modifiers for cyanoacrylate.

One class is a series of terpolymers derived from glycolide and two or more of the following monomers: lactide, ε-caprolactone, dioxanone, and trimethylene carbonate. The monomers are copolymerized in ratios, which yield an amorphous and rubbery copolymer. This is in contrast to typical copolymers used for suture manufacture, which generally possess high degrees of crystallinity in order to be suitable for producing fibers. An additional feature of this class of copolymers is that they contain at least 10% glycolide moiety in their chains, which renders them quickly biodegradable.

The second class of copolymers is a series of copolymers derived from cyanoacrylate and one or more of the following monomers: glycolide, lactide, ε-caprolactone, dioxanone and trimethylene carbonate. The cyanoacrylate may be alkyl 2-cyanoacrylate, alkenyl 2-cyanoacrylate, alkoxyalkyl 2-cyanoacrylate, carbalkoxyalkyl 2-cyanoacrylate. The alkyl group may have 1 to 16 carbon atoms and is preferably a $C_1$–$C_8$ alkyl 2-cyanoacrylate. Suitable cyanoacrylates include, for example, methyl 2-cyanoacrylate, ethyl 2-cyanoacrylate, n-propyl 2-cyanoacrylate, iso-propyl 2-cyanoacrylate, n-butyl 2-cyanoacrylate, iso-butyl 2-cyanoacrylate, hexyl 2-cyanoacrylate, n-octyl 2-cyanoacrylate, 2-octyl 2-cyanoacrylate, 2-methoxyethyl 2-cyanoacrylate, 2-ethoxyethyl 2-cyanoacrylate and 2-propoxyethyl 2-cyanoacrylate.

Catalysts useful in the copolymerization of both types of copolymers include cationic anhydrous catalysts, such as $SnCl_2$, stannous octoate and antimony salts. Other useful catalysts are those described for polymerization of cyclic carbonates in U.S. Pat. No. 3,301,824 to Hostettler, which is incorporated herein by reference.

Suitable initiators for the copolymerization may be selected from a large range of protonic and Lewis acids, amines, phosphines, hydrides, alkoxides, alkali derivatives of alkali and alkaline earth metals, as well as, hydrogen donor substances, such as carboxylic acids, alcohols, glycols and alkanolamines.

The copolymers are obtained by combining the catalyst (s), initiator(s) and monomers, mixing and heating at predetermined temperature and time to ensure polymerization. The resultant copolymer may be post-treated by conventional methods to remove any unreacted monomers.

The bioabsorbable cyanoacrylate adhesives of the present invention are obtained by dissolving one or more of the above-described copolymers into one or more of the above-described cyanoacrylate monomers. Unexpectedly high amounts of copolymer(s) can easily be dissolved into the composition due to the nature of the copolymers. The dissolution may take place by agitation at room temperature or elevated temperature.

The bioabsorbable cyanoacrylate adhesives of the present invention may be stabilized against premature polymerization with anionic and free-radical polymerization inhibitors. Anionic polymerization inhibitors known in the art include, but are not limited to, soluble acidic gases (for example sulfur dioxide), and phosphoric, carboxylic and organic sulphonic acids. Free-radical polymerization inhibitors include, but are not limited to, hydroquinone, t-butyl catechol, hydroxyanisole, butylated hydroxyanisole and butylated hydroxytoluene.

The bioabsorbable cyanoacrylate adhesives of the present invention may contain any additives necessary to impart desired properties to the adhesive, such as viscosity, color, or X-ray opacity. The adhesives may optionally include antimicrobial agents, antibiotics, growth-promoting factors, anti-cancer drugs, immune system enhancing drugs, and leachable inorganic fillers.

For example, dyes contemplated for use in the present invention include, but are not limited to, D&C Violet No. 2, D&C Green No. 6, carbon black and bone black. Growth factors contemplated for use in the adhesives of the present invention include, but are not limited to, fibroblast growth factor, bone growth factor, epidermal growth factor, platelet derived growth factor, macrophage derived growth factor, alveolar derived growth factor, monocyte derived growth factor, magainin, and so forth. Inorganic leachable fillers contemplated for use in the adhesives of the present invention include, but are not limited to, tricalcium phosphate, hydroxyapatite, calcium carbonate, and calcium chloride.

The adhesive compositions of the present invention can be heat sterilized by following the teachings of U.K. Pat. GB 2 306 469B, which patent is incorporated herein by reference.

Accordingly, one embodiment of the invention is directed to copolymers derived from one or more cyanoacrylates and one or more other monomers selected from glycolide, lactide, ε-caprolactone, dioxanone and trimethylene carbonate, wherein the cyanoacrylate is selected from alkyl 2-cyanoacrylate, alkenyl 2-cyanoacrylate, alkoxyalkyl 2-cyanoacrylate, or carbalkoxyalkyl 2-cyanoacrylate, and wherein the alkyl group may have 1 to 16 carbon atoms. Preferably, the cyanoacrylates are selected from methyl 2-cyanoacrylate, ethyl 2-cyanoacrylate, n-propyl 2-cyanoacrylate, iso-propyl 2-cyanoacrylate, n-butyl 2-cyanoacrylate, iso-butyl 2-cyanoacrylate, hexyl 2-cyanoacrylate, n-octyl 2-cyanoacrylate, 2-octyl 2-cyanoacrylate, 2-methoxyethyl 2-cyanoacrylate, 2-ethoxyethyl 2-cyanoacrylate and 2-propoxyethyl 2-cyanoacrylate.

Another embodiment is directed to a bioabsorbable tissue adhesive composition obtained by dissolving the above copolymers into a cyanoacrylate monomer or a blend of cyanoacrylate monomers, wherein the cyanoacrylate monomers are selected from alkyl 2-cyanoacrylate, alkenyl 2-cyanoacrylate, alkoxyalkyl 2-cyanoacrylate, or carbalkoxyalkyl 2-cyanoacrylate, and wherein the alkyl group may have 1 to 16 carbon atoms and may be methyl 2-cyanoacrylate, ethyl 2-cyanoacrylate, n-propyl 2-cyanoacrylate, iso-propyl 2-cyanoacrylate, n-butyl 2-cyanoacrylate, iso-butyl 2-cyanoacrylate, hexyl 2-cyanoacrylate, n-octyl 2-cyanoacrylate, 2-octyl 2-cyanoacrylate, 2-methoxyethyl 2-cyanoacrylate, 2-ethoxyethyl 2-cyanoacrylate and 2-propoxyethyl 2-cyanoacrylate.

Another embodiment is directed to bioabsorbable tissue adhesive compositions obtained by dissolving copolymers derived from glycolide and two other monomers selected from lactide, ε-caprolactone, dioxanone and trimethylene carbonate, the copolymers possessing amorphous structure and being in rubbery state at body temperature, into cyanoacrylate monomer or a blend of cyanoacrylate monomers, wherein the cyanoacrylate monomers are selected from alkyl 2-cyanoacrylate, alkenyl 2-cyanoacrylate, alkoxyalkyl 2-cyanoacrylate, or carbalkoxyalkyl 2-cyanoacrylate, wherein the alkyl group may have 1 to 16 carbon atoms and may be methyl 2-cyanoacrylate, ethyl 2-cyanoacrylate, n-propyl 2-cyanoacrylate, iso-propyl 2-cyanoacrylate, n-butyl 2-cyanoacrylate, iso-butyl 2-cyanoacrylate, hexyl 2-cyanoacrylate, n-octyl 2-cyanoacrylate, 2-octyl 2-cyanoacrylate, 2-methoxyethyl 2-cyanoacrylate, 2-ethoxyethyl 2-cyanoacrylate and 2-propoxyethyl 2-cyanoacrylate.

Applications of the present invention include, but are not limited to, wound closure (including surgical incisions and other wounds), adhesives for medical devices (including implants), sealants and void fillers in human and animal medical applications, and embolic agents.

The following examples are offered to illustrate embodiments of the invention, and should not be viewed as limiting the scope of the invention.

EXAMPLES

Example 1

Preparation and Properties of Amorphous and Rubbery Terpolymers

The monomers, stannous octoate and dodecanol were added to a reactor in quantities as specified in Table 1. The mixture was heated to 165° C. with stirring under nitrogen atmosphere for 24 hours. The reaction product was discharged and treated at 45° C. under vacuum of less than 1 mmHg for 48 hours to remove any unreacted monomers. Glass transition (Tg) of the copolymers was determined by Differential Scanning Calorimetry with heating rate of 20° C./min. As can be seen from Table 1, the synthesized copolymers were completely amorphous with low glass transition points and were rubbery at room temperature.

TABLE 1

Polymerization ratios and properties of copolymers

| Copolymer No. | ε-caprolactone (g) | lactide (g) | glycolide (g) | stannous octoate (g) | dodecanol (g) | Tg (° C.) | Physical appearance of copolymer | Soluble into NBCA |
|---|---|---|---|---|---|---|---|---|
| C1 | 666 | 666 | 666 | 0.4 | 5 | 1.1 | rubbery | yes |
| C2 | 800 | 800 | 400 | 0.4 | 5 | 12.9 | rubbery | yes |
| C3 | 800 | 400 | 800 | 0.4 | 5 | -3.4 | rubbery | yes |
| C4 | 1000 | 500 | 500 | 0.4 | 5 | -16.0 | rubbery | yes |

Example 2

Preparation of Cyanoacrylate Containing Copolymers

Lactide, ε-caprolactone, and glycolide were added to a reactor along with stannous octoate and dodecanol in the amounts specified in Table 2. The mixture was heated to 60° C. with stirring under nitrogen atmosphere. Then the specified amount in Table 2 of n-butyl 2-cyanoacrylate (NBCA) was added into the reactor, and the mixture was heated with stirring under nitrogen atmosphere to 165° C. and kept at 165° C. for 2 hours. The reaction product was discharged and treated under vacuum of less than 1 mmHg at 45° C. for 48 hours to remove any unreacted monomers. Glass transition temperature (Tg) of the copolymers was determined by Differential Scanning Calorimetry with a heating rate of 20° C./min.

TABLE 2

Preparation and properties of cyanoacrylate containing copolymers

| Copolymer No. | NBCA (g) | ε-caprolactone (g) | lactide (g) | glycolide (g) | stannous octoate (g) | dodecanol (g) | Tg (° C.) | Physical appearance of copolymer | Soluble into NBCA |
|---|---|---|---|---|---|---|---|---|---|
| C5 | 333 | 333 | 1000 | 333 | 0.4 | 8 | 20.2 | tough | yes |
| C6 | 466 | 466 | 600 | 466 | 0.4 | 8 | 9.9 | rubbery | yes |

TABLE 2-continued

Preparation and properties of cyanoacrylate containing copolymers

| Copolymer No. | NBCA (g) | ε-caprolactone (g) | lactide (g) | glycolide (g) | stannous octoate (g) | dodecanol (g) | Tg (° C.) | Physical appearance of copolymer | Soluble into NBCA |
|---|---|---|---|---|---|---|---|---|---|
| C7 | 200 | 200 | 1200 | 400 | 0.4 | 8 | 26.3 | glassy | yes |
| C8 | 200 | 600 | 1000 | 200 | 0.4 | 8 | 6.3 | rubbery | yes |

Example 3

Preparation of Adhesives

Bioabsorbable cyanoacrylate tissue adhesive compositions were obtained by mixing by stirring a measured amount of copolymer into n-butyl 2-cyanoacrylate (NBCA) at room temperature for 24 hours. The quantities of copolymers and cyanoacrylate are shown in Table 3. The copolymers were completely dissolved, forming homogeneous, viscous products.

TABLE 3

Adhesive formulations

| Adhesive No. | Quantity of NBCA (g) | Type of copolymer | Quantity of copolymer (g) |
|---|---|---|---|
| A1 | 175 | C1 | 25 |
| A2 | 175 | C3 | 25 |
| A3 | 175 | C4 | 25 |
| A4 | 175 | C6 | 25 |
| A5 | 175 | C8 | 25 |
| A6 | 166 | C3 | 34 |
| A7 | 170 | C6 | 30 |
| A8 | 150 | C6 | 50 |
| A9 | 140 | C6 | 60 |

Example 4

Elasticity of Cured Adhesives

Specimens of 35 mm in length, 6.5 mm in width and 2 mm in thickness were prepared by curing the adhesives in polytetrafluoroethylene molds. Commercially available cyanoacrylate activator Ritelok AC69, Chemence Inc., was used to facilitate bulk polymerization. The specimens were subjected to dynamic mechanical analysis at a frequency of 1 Hz. The value of the modulus of elasticity at 37° C. was recorded. The results presented in Table 4 show that the cured adhesives of the present invention are more than two times more flexible at body temperature than cured unmodified n-butyl 2-cyanoacrylate (NBCA).

TABLE 4

Modulus of elasticity of cured adhesives

| Cured adhesive | E' at 37° C. (10$^8$ Pa) |
|---|---|
| NBCA | 13.8 |
| A1 | 7.2 |
| A2 | 7.3 |
| A3 | 5.9 |
| A4 | 6.9 |
| A5 | 5.5 |
| A8 | 6.4 |

Example 5

Strength Properties of Cured Adhesives

Test specimens were prepared as described in Example 4. They were tested in tensile mode with crosshead speed of 1 mm/min. The peak stress was recorded. N-butyl 2-cyanoacrylate (NBCA), n-hexyl 2-cyanoacrylate (NHCA) and 2-octyl 2-cyanoacrylate (2-OCA) were tested alongside the adhesives of the present invention for comparison. The data presented in Table 5 are averages of 10 measurements. The results show that the adhesives of the present invention possess substantial bulk strength surpassing that of NHCA and 2-OCA.

TABLE 5

Tensile strength properties of cured adhesives

| Cured adhesive | Peak stress (kg/mm$^2$) |
|---|---|
| NBCA | 2.0 |
| NHCA | 0.9 |
| 2-OCA | 0.5 |
| A1 | 1.6 |
| A2 | 0.9 |
| A3 | 1.6 |
| A4 | 1.8 |
| A5 | 1.1 |
| A8 | 1.3 |

Example 6

Tensile Shear Strength of Stainless Steel Bonded Joints

Specimens with dimensions according to ASTM D1002-94 were made of stainless steel. The area to be bonded (see ASTM D1002-94) was roughened with extra-fine sandpaper and degreased with acetone. Adhesive was applied to one surface, which was overlapped with another coupon. The joint was clamped with two bulldog clips and placed at 37° C. for 24 hours. After annealing to room temperature, the joints were tested in tension with crosshead speed of 10 mm/min. The results are averages of 10 tested assemblies each and are presented in Table 6. For comparison purposes joints based on NBCA, NHCA and 2-OCA were tested alongside the adhesives of the present invention. Unexpectedly, the adhesive bonds based on the adhesives of the present invention outperformed those of unmodified cyanoacrylates.

TABLE 6

Tensile shear strength of stainless steel bonded joints

| Adhesive | Tensile shear strength (kg/cm$^2$) |
|---|---|
| NBCA | 94 |
| NHCA | 90 |
| 2-OCA | 82 |

TABLE 6-continued

Tensile shear strength of stainless steel bonded joints

| Adhesive | Tensile shear strength (kg/cm$^2$) |
| --- | --- |
| A7 | 128 |
| A8 | 123 |

Example 7

Set Time of Adhesives

Specimens with dimensions according to ASTM D1002-94 were made of Nylon 6,6. The area to be bonded (see ASTM D1002-94) was degreased with acetone. A drop of adhesive was applied to one surface, which was overlapped with another coupon. The joint was clamped with two bulldog clips. After a measured period of time, in 15-second increments, the clips were removed, and the joint was subjected to 2 kg load. The set time was determined as the time, measured after clamping, when the bonded assembly could withstand a 2 kg weight for 30 seconds. At least 5 consecutively bonded joints had to meet the test requirement in order to establish the set time. The adhesive bonding was performed at 21–22° C. and 55–65% relative humidity. Joints bonded with NBCA, NHCA and 2-OCA were tested for comparison purposes. The results presented in Table 7 show that the adhesives of the present invention have similar set times to unmodified cyanoacrylates.

TABLE 7

Set time of adhesives

| Adhesive | Set time (sec) |
| --- | --- |
| NBCA | 90 |
| NHCA | 90 |
| 2-OCA | 195 |
| A2 | 90 |
| A4 | 90 |
| A6 | 120 |
| A8 | 105 |
| A9 | 120 |

Example 8

In-vitro Strength Loss of Bonded Joints

Pieces of silk braided suture, USP 2, were cut in 10 cm length and were acetone soaked and washed to remove the silicone finish. The suture pieces were left to dry at room temperature for 24 hours. Two pieces of suture were aligned over 2 cm length, clamped at both ends of the overlap with bulldog clips, and one of the clips twisted 180 degrees to the other. A drop of adhesive was spread along the overlap. The assembly was left undisturbed for 2 hours at room temperature and then moved to 37° C. oven for 24 hours. The bonded silk sutures were then placed at 37° C. in Sorensen's buffer solution with pH of 7.2. Following a measured period of time, the bonded sutures were removed from the buffer, washed with deionized water and placed in an oven to dry for 24 hours at 37° C. After annealing to room temperature, the bonded assembly was tested by pulling to failure with 10 mm/min crosshead speed. The data is an average of 10 measurements and is presented in Table 8. The results demonstrate, as expected, an enhanced loss of strength of the adhesives of the present invention with time in "in-vitro" test media.

TABLE 8

In-vitro strength loss of adhesives

| Adhesive | Initial pull strength (kg) | Pull strength following 5 weeks in buffer (kg) | Pull strength following 12 weeks in buffer (kg) |
| --- | --- | --- | --- |
| NBCA | 5.4 | 4.1 | 1.9 |
| A7 | 6.5 | 2.2 | 1.1 |

Example 9

In-vitro Mass Loss of Adhesive Film

Cured adhesive film was prepared by spreading 0.07 g of adhesive on the surface of a microscope glass slide. The adhesive was left to cure. Film with average thickness of 0.045 mm was scraped from the glass slide, placed at 37° C. under vacuum for 4 hours, followed by 12 hours in a desiccator cabinet. Approximately 0.04 g of the film was weighed precisely and placed in Sorensen's buffer solution of pH of 7.2 at 37° C. Samples were removed from the buffer solution at measured periods of time, washed with deionized water, dried at 37° C. under vacuum for 4 hours and placed in a desiccator cabinet for 12 hours. Then the weight of the sample was measured and the weight loss calculated. The results are presented in Table 9. For comparison, films of NBCA, NHCA and 2-OCA were tested alongside the adhesives. The results clearly demonstrate 2 to 19 fold increase in degradability of the adhesives of the present invention compared to unmodified cyanoacrylates. It is expected that at "in-vivo" conditions, the bioabsorbed copolymer phase in the adhesive film will create pathways for tissue growth connecting the bonded surfaces, leading to quicker healing.

TABLE 9

In-vitro weight loss of adhesive film

| | Weight loss (%) after aging in buffer at 37° C. for | | |
| --- | --- | --- | --- |
| Adhesive | 7 weeks | 12 weeks | 20 weeks |
| NBCA | 2.4 | 4.3 | 5.3 |
| NHCA | 0.7 | 1.5 | 2.6 |
| 2-OCA | 0.2 | 0.7 | 1.4 |
| A1 | 6.2 | 13.5 | 16.2 |
| A2 | 10.8 | 15.4 | 17.4 |
| A3 | 7.7 | 8.0 | 10.5 |
| A4 | 6.0 | 14.9 | 18.0 |
| A5 | 5.0 | 8.8 | 10.9 |
| A8 | 8.2 | 21.2 | 26.6 |

Other embodiments and uses of the invention will be apparent to those skilled in the art from consideration of the specification and practice of the invention disclosed herein. All references cited herein, including all U.S. and foreign patents and patent applications, are specifically and entirely incorporated by reference. It is intended that the specification and examples be considered exemplary only, with the true scope and spirit of the invention indicated by the following claims.

What is claimed is:

1. A copolymer derived from one or more cyanoacrylates and one or more other monomers, wherein said one or more cyanoacrylates are selected from the group consisting of alkyl 2-cyanoacrylate, alkenyl 2-cyanoacrylate, alkoxyalkyl 2-cyanoacrylate, and carbalkoxyalkyl 2-cyanoacrylate, wherein the alkyl group of said one or more cyanoacrylates has 1 to 16 carbon atoms, and wherein said one or more other monomers is selected from the group consisting of glycolide, lactide, ε-caprolactone, dioxanone and trimethylene carbonate.

2. The copolymer of claim 1 wherein said one or more cyanoacrylates are selected from the group consisting of methyl 2-cyanoacrylate, ethyl 2-cyanoacrylate, n-propyl 2-cyanoacrylate, iso-propyl 2-cyanoacrylate, n-butyl 2-cyanoacrylate, iso-butyl 2-cyanoacrylate, hexyl 2-cyanoacrylate, n-octyl 2-cyanoacrylate, 2-octyl 2-cyanoacrylate, 2-methoxyethyl 2-cyanoacrylate, 2-ethoxyethyl 2-cyanoacrylate and 2-propoxyethyl 2-cyanoacrylate.

3. A method for making a bioabsorbable adhesive composition comprising the step of dissolving the copolymer of claim 1 into a cyanoacrylate monomer or blend of cyanoacrylate monomers, wherein the cyanoacrylate monomer or monomers are selected from the group consisting of alkyl 2-cyanoacrylate, alkenyl 2-cyanoacrylate, alkoxyalkyl 2-cyanoacrylate, and carbalkoxyalkyl 2-cyanoacrylate, and wherein the alkyl group of said cyanoacrylate monomers has 1 to 16 carbon atoms.

4. The method of claim 3 wherein said cyanoacrylate monomer or monomers having an alkyl group of 1 to 16 carbon atoms are selected from the group consisting of methyl 2-cyanoacrylate, ethyl 2-cyanoacrylate, n-propyl 2-cyanoacrylate, iso-propyl 2-cyanoacrylate, n-butyl 2-cyanoacrylate, isobutyl 2-cyanoacrylate, hexyl 2-cyanoacrylate, n-octyl 2-cyanoacrylate, 2-octyl 2-cyanoacrylate, 2-methoxyethyl 2-cyanoacrylate, 2-ethoxyethyl 2-cyanoacrylate and 2-propoxyethyl 2-cyanoacrylate.

5. A bioabsorbable tissue adhesive made by the method of claim 3.

6. A bioabsorbable adhesive composition comprising the copolymer of claim 1 dissolved into a cyanoacrylate monomer or blend of cyanoacrylate monomers, wherein the cyanoacrylate monomer or monomers are selected from the group consisting of alkyl 2-cyanoacrylate, alkenyl 2-cyanoacrylate, alkoxyalkyl 2-cyanoacrylate, and carbalkoxyalkyl 2-cyanoacrylate, and wherein the alkyl group of said cyanoacrylate monomers has 1 to 16 carbon atoms.

7. The composition of claim 6 wherein said cyanoacrylate monomer or monomers having an alkyl group of 1 to 16 carbon atoms are selected from the group consisting of methyl 2-cyanoacrylate, ethyl 2-cyanoacrylate, n-propyl 2-cyanoacrylate, iso-propyl 2-cyanoacrylate, n-butyl 2-cyanoacrylate, iso-butyl 2-cyanoacrylate, hexyl 2-cyanoacrylate, n-octyl 2-cyanoacrylate, 2-octyl 2-cyanoacrylate, 2-methoxyethyl 2-cyanoacrylate, 2-ethoxyethyl 2-cyanoacrylate and 2-propoxyethyl 2-cyanoacrylate.

8. The composition of claim 6 further comprising one or more additives necessary to impart desired properties to the adhesive, said properties selected from the group consisting of viscosity, color and X-ray opacity.

9. The composition of claim 6 further comprising one or more additives selected from the group consisting of antimicrobial agents, antibiotics, growth-promoting factors, anti-cancer drugs, immune system enhancing drugs, and leachable inorganic fillers.

10. A method for closing a wound comprising the step of applying the composition of claim 6 to said wound.

11. The method of claim 10 wherein the wound is a surgical incision.

12. A method for adhering a medical device to a surface comprising the steps of:
    applying the composition of claim 6 to either or both said device or said surface;
    bringing the device, composition and surface into contact with each other; and
    allowing the composition to set thereby adhering the device and surface to each other.

13. The method of claim 12 wherein said medical device is an implant.

14. An embolic agent comprising the composition of claim 6.

15. A sealant or void filler for use in medical application comprising the composition of claim 6.

16. An adhesive for wound closure comprising the composition of claim 6.

17. A method for making a bioabsorbable adhesive composition comprising the step of dissolving one or more copolymers, said copolymers derived from glycolide and two other monomers, into a cyanoacrylate monomer or blend of cyanoacrylate monomers, wherein said one or more copolymers possess amorphous structure and are in a rubbery state at body temperature, and wherein said two other monomers are selected from the group consisting of lactide, ε-caprolactone, dioxanone and trimethylene carbonate, and wherein the cyanoacrylate monomer or monomers are selected from the group consisting of alkyl 2-cyanoacrylate, alkenyl 2-cyanoacrylate, alkoxyalkyl 2-cyanoacrylate, and carbalkoxyalkyl 2-cyanoacrylate, and wherein the alkyl group of said cyanoacrylate monomers has 1 to 16 carbon atoms.

18. The method of claim 17 wherein the cyanoacrylate monomer or monomers having an alkyl group of 1 to 16 carbon atoms are selected from the group consisting of methyl 2-cyanoacrylate, ethyl 2-cyanoacrylate, n-propyl 2-cyanoacrylate, iso-propyl 2-cyanoacrylate, n-butyl 2-cyanoacrylate, iso-butyl 2-cyanoacrylate, hexyl 2-cyanoacrylate, n-octyl 2-cyanoacrylate, 2-octyl 2-cyanoacrylate, 2-methoxyethyl 2-cyanoacrylate, 2-ethoxyethyl 2-cyanoacrylate and 2-propoxyethyl 2-cyanoacrylate.

19. A bioabsorbable tissue adhesive made by the method of claim 17.

20. A bioabsorbable adhesive composition comprising one or more copolymers, said copolymers derived from glycolide and two other monomers, dissolved into a cyanoacrylate monomer or blend of cyanoacrylate monomers, wherein said one or more copolymers possess amorphous structure and are in a rubbery state at body temperature, and wherein said two other monomers are selected from the group consisting of lactide, ε-caprolactone, dioxanone and trimethylene carbonate, and wherein the cyanoacrylate monomer or monomers are selected from the group consisting of alkyl 2-cyanoacrylate, alkenyl 2-cyanoacrylate, alkoxyalkyl 2-cyanoacrylate, and carbalkoxyalkyl 2-cyanoacrylate, and wherein the alkyl group of said cyanoacrylate monomers has 1 to 16 carbon atoms.

21. The composition of claim 20 wherein the cyanoacrylate monomer or monomers having an alkyl group of 1 to 16 carbon atoms are selected from the group consisting of methyl 2-cyanoacrylate, ethyl 2-cyanoacrylate, n-propyl 2-cyanoacrylate, iso-propyl 2-cyanoacrylate, n-butyl 2-cyanoacrylate, iso-butyl 2-cyanoacrylate, hexyl 2-cyanoacrylate, n-octyl 2-cyanoacrylate, 2-octyl 2-cyanoacrylate, 2-methoxyethyl 2-cyanoacrylate, 2-ethoxyethyl 2-cyanoacrylate and 2-propoxyethyl 2-cyanoacrylate.

22. The composition of claim 20 further comprising one or more additives necessary to impart desired properties to the adhesive, said properties selected from the group consisting of viscosity, color and X-ray opacity.

23. The composition of claim 20 further comprising one or more additives selected from the group consisting of antimicrobial agents, antibiotics, growth-promoting factors, anti-cancer drugs, immune system enhancing drugs, and leachable inorganic fillers.

24. A method for closing a wound comprising the step of applying the composition of claim 20 to said wound.

25. The method of claim 24 wherein the wound is a surgical incision.

26. A method for adhering a medical device to a surface comprising the steps of:

applying the composition of claim 20 to either or both said device or said surface;

bringing the device, composition and surface into contact with each other; and allowing the composition to set thereby adhering the device and surface to each other.

27. The method of claim 26 wherein said medical device is an implant.

28. An embolic agent comprising the composition of claim 20.

29. A sealant or void filler for use in medical applications comprising the composition of claim 20.

30. An adhesive for wound closure comprising the composition of claim 20.

* * * * *